United States Patent [19]

Leiner et al.

[11] Patent Number: 4,730,054
[45] Date of Patent: Mar. 8, 1988

[54] IMIDAZOLE THIENO-BENZOTHIEPINS

[75] Inventors: Jan Leiner; Vladislava Holá; Miroslav Rajsner; Iva Matunová, all of Prague, Czechoslovakia

[73] Assignee: SPOFA, Spojene Podinky Pro Zdravotnickou Vyrobu, Prague, Czechoslovakia

[21] Appl. No.: 936,540

[22] Filed: Dec. 1, 1986

[30] Foreign Application Priority Data

Nov. 29, 1985 [CS] Czechoslovakia ............ 8664-85

[51] Int. Cl.⁴ ..................................... C07D 495/04
[52] U.S. Cl. ................................. 548/336; 549/12
[58] Field of Search ................................. 548/336

[56] References Cited

U.S. PATENT DOCUMENTS 4,169,205  9/1979  Hoehn .......................... 548/336

OTHER PUBLICATIONS

Derwent Abstract of Japan 56073073 6/17/81.

Primary Examiner—Richard A. Schwartz

[57] ABSTRACT

The present invention relates to imidazolyl thieno-benzothiepin derivatives of the Formula I:

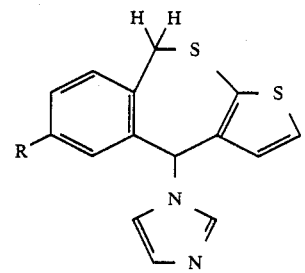

and acid addition salts thereof with pharmaceutically acceptable inorganic and organic acids, wherein R is a hydrogen or a chlorine atom. The invention also relates to processes for the preparation of these compounds. These compounds demonstrate substantial in vitro and in vivo antimycotic properties of the kind useful for the treatment of dermal and vaginal mycoses.

The new compounds can be prepared by reacting 4,9-dihydrothieno(2,3-c)-2-benzothiepin-4-ol or its 6-chloro derivative with imidazole or a reactive derivative thereof, such as 1,1'-carbonyl-diimidazole or 1,1'-thionyldiimidazole; or by first converting the respective thieno-benzothiepin-4-ol into its alkane- or arenesulfonate ester, followed by reaction with imidazole.

5 Claims, No Drawings

IMIDAZOLE THIENO-BENZOTHIEPINS

The present invention relates to imidazolyl thieno-benzothiepin derivatives of the Formula I:

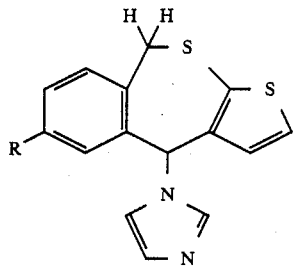

and acid addition salts thereof with pharmaceutically acceptable inorganic and organic acids, wherein R is a hydrogen or a chlorine atom. The invention also relates to processes for the preparation of these compounds. These compounds demonstrate substantial in vitro and in vivo antimycotic properties of the kind useful for the treatment of dermal and vaginal mycoses.

The new compounds can be prepared by reacting 4,9-dihydrothieno(2,3-c)-2-benzothiepin-4-ol or its 6-chloro derivative with imidazole or a reactive derivative thereof, such as 1,1'-carbonyl-diimidazole or 1,1'-thionyldiimidazole; or by first converting the respective thieno-benzothiepin-4-ol into its alkane- or arenesulfonate ester, followed by reaction with imidazole.

BACKGROUND OF THE INVENTION

Mycotic infections are serious dermal conditions of considerable clinical importance. These infections are often debilitating, and they often result in death. Efforts to combat such diseases include the recent and continuing use of a growing number of therapeutic agents and methods, such as antibiotics, cytostatics, immunosuppressive agents and hormonal therapy. There is a rising incidence of vaginal mycosis cases, and the most frequently observed etiological factors known to induce dermal and related infections are pathogenic yeasts and molds. Therapy for epidermal and gynecological mycoses has become difficult, because of the wide variety of infectious agents and a rapidly developing resistance to treatment. Despite the increasing introduction of numerous antimycotic agents having diverse chemical structures and modes of action, there remains a consistent shortage of potent, reliable and safe remedies for the prevention and cure of mycotic infections.

SUMMARY OF THE INVENTION

It has recently been discovered that the inventive imidazolyl thieno-benzothiepins of Formula I and their acid addition salts possess remarkable antimycotic properties. For example, the new compounds were compared in vitro with the known antimycotic agents clotrimazole, miconazole and ketoconazole, in order to determine their minimum inhibitive concentrations (MICs). See, Fromtling, R. A., "Imidazoles as medically important antifungal agents: an overview," 20 Drugs of Today No. 7, 328-331 (1984); Burgess & Bodey, "Clotrimazole," 2 Antimicrobial Agents and Chemotherapy No. 6, 423-6 (1972). MIC values were determined by the standard dilution method in a liquid nutrient medium, primarily with the following yeast and mold species typically used in preliminary antimycotic screening: Saccharomuces pastorianus, Candida albicans, Trichophyton mentagrophytes, and Aspergillus niger. The test innoculum size was $10^6$ CFU/ml for Aspergillus niger and Trichophyton mentagrophytes and $10^4$ CFU/ml for Saccharomuces pastorianus and Candida albicans, where CFU is the standard abbreviation for microbial cell counts.

The results of this comparison are summarized in TABLE I.

TABLE I

Inventive Compounds Ia and Ib, and Known Antimycotic Agents: Antimycotic Activity (MIC) in mg/l For Various Yeasts and Molds

| Compound | S pastorianus | C albicans | T mentagrophytes | A niger |
|---|---|---|---|---|
| Ia (R = H) VUFB 15018 | 25 | 25 | 1.5 | 0.7 |
| Ib (R = Cl) VUFB 16208 | 12.5 | 3.1 | 0.03 | 0.03 |
| Clotrimazole | 3.1 | 0.7 | 0.03 | 3.1 |
| Miconazole | 6.2 | 0.7 | 0.03 | 1.5 |
| Ketoconazole | 50 | 0.03 | 0.7 | 12.5 |

The sensitivity of a larger number of clinical strain isolates of pathogenic molds (a total of 16) as well as yeasts and related microorganisms (a total of 21) when exposed to the inventive compounds was determined using the dilution method on Sabouraud agar. Thus, the experimental MIC values for mold strains exposed to Compound Ia were from 0.7 to 100 mg/l. MIC values for mold strains exposed to Compound Ib were from 0.01 to 1.5 mg/l. MIC values for mold strains exposed to clotrimazole, the most potent of the antimycotic agents tested, were also from 0.01 to 1.5 mg/l. The addition of serum or blood to the ager test plate doubled the effect of compound Ia, had no effect on compound Ib, and diminished the effect of clotrimazole about one third—in comparison to the protein-free agar culture values.

The in vivo evaluation of antimycotic activity was performed using a model of vaginal candidosis induced experimentally in mice by Candida albicans. The test substances were administered intravaginally over a period of ten days in the form of homogenized suspensions of appropriately chosen concentrations in a 0.5% aqueous hydroxyethylcellulose solution. The results were evaluated both immediately upon administration and after one and two weeks. Compound Ia elicited complete inhibition of the test culture at a concentration of 7.5%, both in therapy starting 24 hours prior to and simultaneously with the experimental infection, i.e., the compound also demonstrated a significant prophylactic (preventative) effect. The results were somewhat less favorable in all of the tests when therapy was delayed until 24 hours after infection.

Among the inventive compounds Ia and Ib, compound Ib, designated as "clopinazole," is preferred. When compared with clotrimazole and miconazole, the most potent known antimycotic agents derived from imidazole, clopinazole demonstrated a similarly potent level of activity against typical inducers of dermal mycoses, and a notably increased activity against Aspergillus strains. Moreover, the potency of the new compound is not diminished by the presence of biological protein substances, such as blood constituents.

Experimental treatment of vaginal Candida albicans infections in mice confirm the beneficial therapeutic effect of the compound upon topical application. Minimum MIC values for clopinazole, in dilution tests on Sabouraud agar, for about forty pathogenic yeast and mold strains, ranged from 0.01 to 25 mg/l. The compound is only slightly toxic. Its $LD_{50}$ in female and male rats was 1125 and 1570 mg/kg p.o., respectively. The standard tests for mutagenity, cancerogenity, teratogenity, foetal damage, dermal and vaginal irritation, as well as chronic (one month) toxicity in rat and dog on intravaginal administration were all negative.

These in vivo and in vitro test results indicate that the inventive compounds, and clopinazole in particular, are useful for the treatment of epidermal and epithelial (e.g., vaginal) mycoses in mammals. For therapeutic applications, the active compounds can be advantageously combined with known pharmaceutical excipients to provide convenient topical and oral dosage forms, such as solutions, suspensions, gels, creams, ointments, powders, tablets, capsules, and sprays, etc. These dosage forms contain the active ingredient, preferably in a quantity of from 1 to 10% by weight.

The present compounds benefit from a newly discovered and advantageous structural skeleton attached to the imidazolyl moeity (a 1-imidazolyl radical). The predominant portion of the new compound comprises a tricyclic heterocyclic skeleton, unlike the primarily isocyclic skeleton (a single aromatic nuclei with minor aliphatic links) known in the art. A small number of known antimycotic agents employ a single heterocyclic residue, but these differ from the present structure. See, e.g., Fromtling and Burgess et al., supra. In addition, the tricyclic heterocyclic skeleton employed herein has heretofore been known only in connection with pharmaceutical agents having completely different and unrelated properties, namely, in connection with the central nervous system. [cite].

As demonstrated by the clinical results summarized in Table I, the present compounds, and the 6-chloro derivative of compound Ib in particular, exhibit a remarkably pronounced activity towards typical strains of *Aspergillus niger* at unrestricted widths of the activity spectrum; and the compounds are markedly effective against other microbial vectors of dermal mycoses as well. The new compounds are particularly advantageous, because, unlike the known compounds, their activity is not diminished in the presence of proteins in biological fluids, such as blood serum and blood components. Indeed, the activity of Compound Ia is actually improved in the presence of these proteins.

In addition, vaginal mycoses are frequently occurring diseases which are difficult to master therapeutically, because of microbial resistance to known medications. As a result, there is a pressing need for new therapeutic compounds which are potent, and which are active against resistant strains. The search for new compounds has been handicapped in the past, because the in vivo and in vitro potency data for the known compounds is imprecise, due to the negative influence of blood proteins on their antimycotic activity. The new compounds do not suffer from this disadvantage.

DETAILED DESCRIPTION

The imidazolyl thieno-benzothiepin compounds of the invention, namely 4-(1-imidazolyl)-4,9-dihydrothieno(2,3-c)-2-benzothiepin. Compound Ia, and 6-chloro-4-(1-imidazolyl)-4,9-dihydrothieno(2,3-c)-2-benzothiepin, Compound Ib, and their acid addition salts can be prepared by several related methods that comprise reacting the respective thieno-benzothiepin-4-ol of Formula II

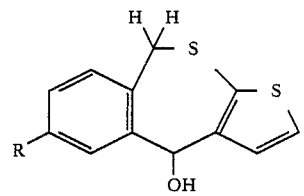

wherein R is a hydrogen or a chlorine atom, or its alkane- or arenesulfonate ester, with imidazole or a reactive derivative thereof, preferably in the presence of an inert organic solvent, followed by subsequent neutralization of the resulting base with a pharmaceutically acceptable organic or inorganic base, to form an addition addition salt as desired.

The starting material 4,9-dihydrothieno(2,3-c)-2-benzothiepin-4-ol is known. M. Rajsner, et al., 32 Coll. Czech. Chem. Commun. 2864 (1967). The alternative chlorinated form can be obtained by reduction of 6-chloro-thieno(2,3-c)-2-benzothiepin-4(9H)-one (idem, 1.c) with hydride reducing agents, such as sodium borohydride in methanol or ethanol.

The reaction of the thieno-benzothiepin-4-ol starting materials of Formula II with imidazole is performed by heating a mixture of these reactants for a period of 2 to 5 hours at 140 to 170 degrees C., or by refluxing a solution of the mixture for 3 to 5 hours in a higher-boiling solvent, such as commercial xylene, at the boiling temperature. After optional removal of the solvent, the product is isolated and purified by crystallization, for example from toluene.

In another embodiment of the process, the starting materials can be first be reacted with alkane- or arenesulfonylchloride, for example, p-toluene-sulfonylchloride, in the presence of an alkaline agent able to bind the hydrogen chloride formed, to yield a reactive alkane- or arenesulfonyl ester. The alkaline agent is preferably anhydrous pyridine. The resulting activated ester intermediate is then reacted in situ with free imidazole. The product is isolated by diluting the reaction mixture with water, extraction via an appropriate solvent, such as chloroform, removal of the solvent, and crystallization of the residue.

In yet another embodiment, the thieno-benzothiepin-4-ol starting material can be reacted with 1,1'-carbonyldiimidazole in an anhydrous aromatic hydrocarbon, (e.g., benzene or toluene), a chlorinated alkane, (e.g. chloroform, dichloromethane or 1,2-dichloroethane), an aliphatic or cyclic ether (e.g., tetrahydrofuran) or an aliphatic nitrile (e.g., acetonitrile) at a temperature of from 10 to 60 degrees C.

The product is isolated either by admixing or emulsifying the reaction mixture in water and subsequently distilling off the solvent from the separated organic portion (the crude product in solution), or vice verse, by removing the solvent from the whole reaction mixture and then emulsifying the residue in an mixture of water and an appropriate organic solvent, e.g., ether or toluene, during which operation the product is crystallized.

In yet another embodiment, the thieno-benzothiepin-4-ol starting material can be reacted with 1,1'-thionyldiimidazole, which is preferably formed immediately in the reaction mixture from imidazole and thionylchloride. The thionylchloride is dropped into a stirred solution or suspension of imidazole in an anhydrous organic solvent, such as aromatic hydrocarbon (e.g., benzene or toluene), a chlorinated alkane, (e.g. chloroform, dichloromethane or 1,2-dichloroethane), or an aliphatic nitrile (e.g., acetonitrile) at a temperature of from 10 to 25 degrees C. The product is isolated as set forth in the preceding paragraph.

In yet another embodiment, the thieno-benzothiepin-4-ol starting material can be reacted with an organophosphorous agent, such as (a) tris (1-imidazolyl)phosphine, prepared by reacting imidazole with phosphorous trichloride. (b) penta(1-imidazolyl)phosphoran, prepared by reacting imidazole with phosphorous pentachloride, or (c) 1,1',1''-phosphonyltriimidazole, obtained in situ by reacting imidazole with phosphonyl chloride. The required imidazole derivative can be obtained for use in the organophosphorous process by dropping a chloroform solution of imidazole into a solution of the corresponding phosphorous chloride reagent, in the same solvent, while stirring and cooling the reaction mixture to a temperature of from −5 to 10 degrees C. A chloroform solution of the thieno-benzothiepin-4-ol starting material is admixed, and the solvent is then removed under reduced pressure, and is replaced by an inert solvent with a higher boiling temperature, preferably dimethylformamide. The reaction is completed by heating for 1 to 3 hours at 120 to 140 degrees C. The product is isolated upon cooling by pouring the reaction mixture into water, extraction with an organic solvent, e.g. chloroform, and evaporation of the volatiles, preferably under reduced pressure.

The resulting crude products are purified either by crystallization from appropriate solvents, such as methanol, ethanol, toluene, or a methanol-ether mixture. If desired, the products can be neutralized with a pharmaceutically acceptable inorganic or organic acid to form an acid addition salt by conventional methods, such as alkalization of an aqueous suspension with an alkali metal hydroxides or carbonates, followed first by isolation via extraction with a suitable solvent, such a chloroform, and second by evaporation.

EXAMPLES

The invention is further described in the following examples, which are illustrative in nature and do not serve to limit the scope of the invention or the appended claims.

EXAMPLE 1

4-(1-Imidazolyl)-4,9-dihydrothieno(2,3-c)-2-benzothiepin

Method A 4,9-Dihydrothieno (2,3-c)-2-benzothiepin-4-ol(23.4 g) is dissolved by gentle warming to about 30° C. in 750 ml of anhydrous benzene. The obtained solution is cooled to 20° C., 1,1'-carbonyldiimidazole (32.4 g) is added in one portion under stirring, and the mixture is stirred for 10 minutes at the same temperature. During the next 15 minutes, the temperature is raised to 60° C., and thereafter the reaction mixture is allowed to cool slowly to 20° C. and is stirred at this temperature for 6 hours. Benzene is distilled off under reduced pressure and the residue is mixed with a water (300 ml) - ether (200 ml) system. Crystals of the product (26.4 g, 86.6% of theory) are separated and dried. The substance has a melting point of 175° to 177° C. Recrystallization from benzene or methanol yields the analytically pure compound; its melting point is unchanged.

Method B 7.3 ml of thionylchloride is dropped into a solution of imidazole (27.2 g) in anhydrous acetonitrile (300 ml) under stirring and ice water cooling to 10° C. during a period of about 20 minutes. The mixture is stirred for 10 minutes at 10° C. and treated portionwise for 5 additional minutes under continued stirring and cooling with 4,9-dihydrothieno(2,3-c)-2-benzothiepin-4-ol (23.4 g), while the temperature of the mixture is maintained between 10° and 14° C. by external ice and water cooling. The reaction mixture is stirred at this temperature for 4 hours. Thereafter, the cooling bath is removed and the mixture is allowed to stand for about 16 hours, it concentrated under reduced pressure to a volume of about 50 ml, and is diluted with 100 ml of water. The crystalline precipitate is dissolved in chloroform (100 ml), the chloroform solution is washed with water (50 ml), dried over anhydrous sodium sulfate and the solvent is evaporated under reduced pressure. The solid residue (26.8 g, melting point 162° to 170° C.) is crystallized from methanol to give the pure product (15.1 g, 53.2% of theory) with a melting point of 174.5 to 176.5° C. Acidification of the methanolic solution with nitric acid and admixture with ether yields crystalline nitrate salt, melting point 143° to 146° C. (from methanol - ether).

Method C

A mixture of 4.9-dihydrothieno(2,3-c)-2-benzothiepin-4-ol (2.3 g) and imidazole (1.4 g) is heated for 2 hours at 160° C. (bath temperature). The obtained dark melt is cooled and mixed with toluene (5 ml), and the so formed crystals are separated and washed successively with this solvent (50 ml) and water to give the title product (1.8 g, 63.4% of theory) with a melting point of 172° to 175° C. The material can be further purified if required by crystallization from methanol.

Method D

To a solution of phosphorus trichloride (1.4 g) in dry chloroform (30 ml) is added, under stirring and cooling to a temperature of −5° to 0° C. during 1 hour, a solution of imidazole (1.4 g) in the same solvent (20 ml). The mixture is allowed to warm spontaneously to about 20° C. and stirring is continued at this temperature for 1 hour. Thereafter a solution of 4,9-dihydrothieno (2,3-c)-2-benzothiepin-4-ol (2.3 g) in dry chloroform (20 ml) is added with continued stirring, whereupon the mixture is stirred for 20 minutes and the solvent is removed under reduced pressure. The residue is refluxed for 2 hours at 130° C. with dimethylformamide (20 ml). After cooling the mixture is diluted with water (150 ml), the product is shaken into chloroform (100 ml), the organic extract is washed with water, dried over anhydrous sodium sulfate, the solvent is evaporated under reduced pressure to a final volume of about 5 ml and the oily residue is allowed to crystallize to give the crude product (1.2 g) melting at 174° to 176° C. Concentration of the mother liquor yields a further 0.7 g of product.

Method E

To a solution of phosphorus pentachloride (2.1 g) in dry chloroform (40 ml), during about 30 minutes under stirring and cooling to a temperature of 0 to 5° C., is dropped a solution of imidazole (6.8 g) in the same solvent (20 ml). The reaction mixture is allowed to warm to about 20° C., stirring is continued at this temperature for 1 hour and a solution of 4,9-dihydrothieno (2,3-c)-2-benzothiepin-4-ol(2,3 g) in the same solvent (20 ml) is added. The solvent is distilled off under reduced pressure, the residue is mixed with anhydrous dimethylformamide (20 ml), and the mixture is refluxed for 2 hours at 130° C. (bath) and diluted with 150 ml of water. The product is shaken into chloroform (100 ml), the organic portion is washed with water, dried over anhydrous sodium sulfate and is evaporated under reduced pressure to a small volume (about 5 ml). The crystalline product (1.9 g) melts at 173° to 176° C.

Method F

A solution of phosphonylchloride (1.5 g) in dry chloroform (30 ml) is treated dropwise during 1 hour under stirring and cooling to a temperature of 0° to 5° C. with a solution of imidazole (4.1 g) in the same solvent (25 ml). The temperature is then allowed to rise to about 20° C., a solution of 4,9-dihydrothieno (2,3-c)-2-benzothiepin-4-ol (2.3 g) in dry chloroform (20 ml) is added with stirring, and after an additional 20 minutes of continued stirring the solvent is removed under reduced pressure. The residue is admixed with anhydrous dimethylformamide (20 ml) and the mixture is heated for 2 hours at a bath temperature of 130° C. Thereafter, 150 ml of water is added, the product is shaken into chloroform, the organic portion is washed with water, dried over anhydrous sodium sulfate and the solvent is distilled off under reduced pressure. The residue is mixed with 5 ml of toluene, and the formed crystals are separated and washed with a small volume of the same solvent to yield 2.0 g (70.4% of theory) of the title product, melting point 174° to 177° C.

Method G

To a solution of 4,9-dihydrothieno(2,3-c-2-benzothiepin-4-ol (2.3 g) in anhydrous pyridine (30 ml) is added in one portion under stirring 1.9 g of p-toluenesulfonylchloride, and the mixture is stored for about 16 hours at room temperature. Thereafter 1.4 g of imidazole is added and the new mixture is stored for another 16 hour period at 20° to 25° C. Then, the reaction mixture is diluted with about 50 ml of water, the product is shaken into chloroform, the organic layer is washed with water and dried over anhydrous sodium sulfate, and the solvent is removed under reduced pressure. The residue is mixed with about 5 ml of toluene, and the crystalline product is separated and washed with a small amount of toluene to yield 0.8 g of the compound melting at 172° to 174° C.

EXAMPLE 2

6-Chloro-4-(1-imidazolyl)-4,9-dihydrothieno(2,3-c)-2-benzothiepin

Method A

6-Chloro-4,9-dihydrothieno(2,3-c)-2-benzothiepin-4-ol (8.0 g) is dissolved in 230 ml of dry benzene by warming to about 50° C. in 230 ml of dry benzene. The solution is cooled to 20° C. and 1,1'-carbonyldiimidazole (9.7 g) is added thereto in one portion under stirring. The reaction mixture is stirred for 4 hours, then 50 ml of water is added and the organic phase is separated, washed with another 50 ml water portion, dried over anhydrous sodium sulfate, and the solvent is removed under reduced pressure. The residue is diluted with hexane (50 ml), and the resulting crystalline precipitate of the product is separated and washed with 10 ml of the same diluent. The yield is 7.4 g (78% of theory) of product melting at 147° to 150° C. Further purification is possible by crystallization, e.g. from toluene.

Method B

A solution of imidazole (54.5 g) in anhydrous 1,2-dichloroethane (600 ml) is treated dropwise for about 10 minutes under stirring and cooling to a temperature of 16° to 18° C. with thionylchloride (23.8 g). The reaction mixture, in which imidazole hydrochloride precipitates, is stirred for 20 minutes at 18° C. During an additional 5 minutes, 53.8 g of 6-chloro-4,9-dihydrothieno(2,3-c)-2-benzothiepin-4-ol is added portionwise while maintaining the temperature between 20° and 25° C. by cooling with water. The reaction mixture is stirred within the same temperature range for 6 hours and then it is allowed to stand for 16 hours. Thereafter, it is diluted with 500 ml of water and the separated organic phase is washed twice with 500 ml of water, dried over anhydrous sodium sulfate, filtered with active carbon, evaporated under reduced pressure to a volume of about 70 ml and allowed to stand for about 3 hours to crystallize. The crystals are collected by filtration and are washed successively with toluene (20 ml) and hexane to give 45.6 g (71.5% of theory) of the pure product melting at 150° to 152° C. Analytically pure compound crystallizes from toluene and has the same melting temperature.

A nitrate salt of the title compound is obtained by acidification of a solution of the base, e.g. in chloroform with a mixture of 65% nitric acid and ethanol, and purified by crystallization from 2-propanol. The salt has a melting point of 160° to 161° C.

The required starting material, 6-chloro-4,9-dihydrothieno-(2,3-c)-2-benzothiepin-4-ol, which also is a novel compound, can be prepared by the following procedure.

6-Chlorothieno(2,3-c)-2-benzothiepin-4(9H)-one (53.3 g) is suspended in methanol (700 ml), and sodium borohydride (7.8 g) is added under stirring within about 1 hour. The reaction mixture is stirred for 3 more hours and thereafter allowed to stand at 20° to 25° C. Crystals of the product are separated and washed successively with methanol (20 ml) and water (70 ml) to give 35.1 g of the crude product. The filtrate is evaporated to a volume of about 300 ml and diluted with water (500 ml) to afford product crystals (17.1 g). The total yield of the resulting intermediate is 52.2 g (97.1% of theory), melting point 153° to 158° C. An analytical sample recrystalized from benzene-petroleum ether or from toluene has a melting point of 156° to 158° C.

The pharmaceutical composition of the invention may be administered for dermatological purposes as an ointment or creme containing from 1 to 2 percent of the active ingredient. For gynecological or intravaginal use, the composition may be administered in combination with known auxilliaries, preferably as a gel, having approximately 5 percent of the active ingredient. The standard dosage is approximately 5 to 9 ml per application, once daily, for about one week.

We claim:

1. An imidazolyl thieno-benzothiepin derivative of the formula

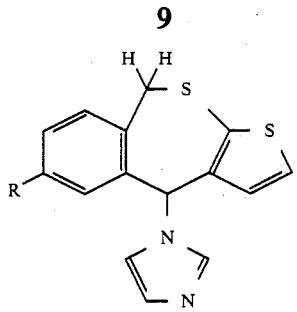
wherein R is selected from the group consisting of a hydrogen and a chlorine atom.
2. 4-(1-imidazolyl)-4,9-dihydrothieno(2,3-c)-2-benzothiepin.
3. 6-chloro-4-(1-imidazolyl)-4,9-dihydrothieno(2,3-c)-2-benzothiepin.
4. A compound of claim 1, in the form of its acid addition salt with a pharmaceutically acceptable organic or inorganic acid.
5. A compound of claim 1, in the form of its nitrate addition salt.
* * * * *